(12) United States Patent
Biernat et al.

(10) Patent No.: US 12,201,621 B2
(45) Date of Patent: Jan. 21, 2025

(54) BASE AND PHARMACEUTICAL COMPOSITION CONTAINING IT

(71) Applicant: BIOTTS S.A., Wroclaw (PL)

(72) Inventors: Pawel Biernat, Wroclaw (PL); Jan Meler, Smolec (PL); Konrad Krajewski, Olawa (PL); Dawid Bursa, Wroclaw (PL)

(73) Assignee: BIOTTS S.A., Wroclaw (PL)

(*) Notice: Subject to any disclaimer, the term of this patent is extended or adjusted under 35 U.S.C. 154(b) by 602 days.

(21) Appl. No.: 16/963,532

(22) PCT Filed: Jul. 9, 2020

(86) PCT No.: PCT/PL2020/050050
§ 371 (c)(1),
(2) Date: Jul. 21, 2020

(87) PCT Pub. No.: WO2021/006753
PCT Pub. Date: Jan. 14, 2021

(65) Prior Publication Data
US 2021/0401817 A1 Dec. 30, 2021

(30) Foreign Application Priority Data
Jul. 9, 2019 (PL) .......................... 430531

(51) Int. Cl.
| | | |
|---|---|---|
| *A61K 31/445* | (2006.01) | |
| *A61K 31/167* | (2006.01) | |
| *A61K 31/196* | (2006.01) | |
| *A61K 47/10* | (2017.01) | |
| *A61K 47/12* | (2006.01) | |
| *A61K 47/44* | (2017.01) | |

(52) U.S. Cl.
CPC .......... *A61K 31/445* (2013.01); *A61K 31/167* (2013.01); *A61K 31/196* (2013.01); *A61K 47/10* (2013.01); *A61K 47/12* (2013.01); *A61K 47/44* (2013.01)

(58) Field of Classification Search
CPC .. A61K 31/445; A61K 31/167; A61K 31/196; A61K 47/10; A61K 47/12; A61K 47/44; A61K 2800/10; A61K 8/34; A61K 8/345; A61K 8/361; A61K 8/46; A61K 8/925; A61K 9/0014; A61K 31/245; A61K 47/18; A61K 47/20; A61K 8/42; A61K 9/06; A61P 23/02; A61Q 19/00
See application file for complete search history.

(56) References Cited

U.S. PATENT DOCUMENTS

| | | | |
|---|---|---|---|
| 4,265,883 A | | 5/1981 | Cameron |
| 5,814,659 A | * | 9/1998 | Elden ................. A61K 31/5375 514/552 |
| 6,268,355 B1 | * | 7/2001 | Mizobuchi ........... A61K 31/616 514/557 |
| 2002/0197284 A1 | * | 12/2002 | Luo ....................... A61K 31/60 424/400 |
| 2003/0082214 A1 | * | 5/2003 | Williams ................ A61P 29/00 514/217 |

FOREIGN PATENT DOCUMENTS

| | | |
|---|---|---|
| CN | 1084068 A | 3/1994 |
| DE | 3811461 A1 | 11/1988 |
| GB | 315306 A | 5/1930 |
| UA | 83402 C2 | 7/2008 |
| WO | 2004/110423 A1 | 12/2004 |

OTHER PUBLICATIONS

Search Report of Polish Patent Office in Polish Application No. P.430531, dated Oct. 10, 2019.
English language translation of Search Report of Polish Patent Office in Polish Application No. P.430531, dated Oct. 10, 2019.
Visegrad Patent Institute / Branch Office PL, International Search Report of International Application PCT/PL2020/050050, dated Oct. 29, 2020.
Visegrad Patent Institute / Branch Office PL, Written Opinion of the International Searching Authority of International Application PCT/PL2020/050050, dated Oct. 28, 2020.

\* cited by examiner

*Primary Examiner* — David Browe (74) *Attorney, Agent, or Firm* — Arrigo, Lee, Guttman & Mouta-Bellum LLP (57) ABSTRACT

The invention relates to a pharmaceutical composition for the delivery of anaesthetic active substances. The pharmaceutical composition contains an anaesthetic active substance, an animal fat, and an anhydrous pharmaceutical ointment base. The anhydrous pharmaceutical ointment base can contain a sulfoxide, a carbonic acid amide, a dihydric alcohol, an aliphatic alcohol, and an omega-9 monounsaturated fatty acid.

8 Claims, 1 Drawing Sheet

BASE AND PHARMACEUTICAL COMPOSITION CONTAINING IT

BACKGROUND OF THE INVENTION

Field of the Invention

The invention relates to a base and a pharmaceutical composition containing it. The invention is applicable to pharmacy.

The present invention relates to an ointment that is effective in the skin anesthesia, prior to procedures that require the reduction of skin sensitivity to pain, such as venipuncture and venous catheterization, blood sampling for testing, and prior to superficial (skin) surgery in adults as well as in children and adolescents. The ointment is made of lidocaine hydrochloride and tetracaine hydrochloride.

Description of Related Art

A cutaneous composition containing tetracaine, lidocaine, based on polyvinyl water, sorbate alcohol, monopalmitic or monostearate sorbate, calcium phosphate and petroleum jelly, is known from US patent U.S. Pat. No. 9,693,976. In the above-mentioned patent (U.S. Pat. No. 9,693,976), the authors use the phenomenon of creating a W/O (water in oil) emulsion with water micromicelles (dispersed phase), petroleum jelly—a lipophilic base (dispersing phase) and emulsifiers (monopalmitic sorbate or monostearate sorbate) located at the interface. The preparation of such an emulsion facilitates the absorption of micromicells, on the surface of which there is a coating made of emulsifier particles and inside there is a hydrophilic (water) phase. The drawback of this solution is the use of anesthetic substances in the base form (as a base), because these forms are soluble in the dissipative, fat phase of the base (petroleum jelly), i.e. in the layer remaining on the skin surface and not absorbed into the deeper layers, where the ends of nerve cells are located. A cream containing lidocaine and tetracaine based on carboxymethylcellulose, polyethylene glycol, glycerin and propanediol is known from the Chinese patent application CN108272746. The authors of patent application CN108272746 used CMC (carboxymethylcellulose), a polymeric substance having both gelling properties and very strong adsorbing properties, to prepare their formulation in the form of a cream/gel.

Carboxymethylcellulose is a synthetic derivative of cellulose that strongly bind smaller molecules, e.g. lidocaine and tetracaine, which, combined with the fact that the CMC polymer molecules are not absorbed by the outer layer of the skin (the stratum corneum), hinders the absorption of active substances, such as lidocaine and tetracaine into the deeper layers where nerve cells are located. A composition is known from US application US2013079404, comprising (i) an active agent selected from at least lidocaine and tetracaine; (ii) the first compound and (iii) a second compound, in which the first compound and the second compound are different and each is selected from the group consisting of N-lauroyl sarcosine, sodium octyl sulfate, methyl laurate, isopropyl myristate, oleic acid, glyceryl oleate and sodium lauryl sulfoacetate. The authors of the patent application US2013079404 used as emulsifiers i.a. sodium octyl sulfate—a highly reactive tenside (surfactant) used in the chemical industry for the production of fluorinated fire-fighting foams and plastic windows cleaning agents. In their formulation, they also used a methyl derivative of lauric acid used as a solvent in gas chromatography. It is also a strong hardening substance with a melting point of 5 deg. C, which, despite the emulsifying properties, makes it very difficult for active substances to reach the target site.

A composition of lidocaine, prilocaine and tetracaine is known from the US application US20061409886, containing 1.5% of lidocaine base; 1.5% of prilocaine base; 4% of tetracaine base; 10% of methylpyrrolidone; 2% of dimethylsulfoxide; 0.08% of topical hyaluronidase; 1.5% of guar gum; 1% of Tween-20; 0.5% of Tween-80 and the necessary amount of water to make up to 100%.

The authors of the application developed a mixture of water-soluble salts of lidocaine, tetracaine and prilocaine as active substances, and excipients being a mixture of emulsifiers-surfactants (guar gum; Tween-20; Tween-80) and solvents (DMSO, water) and hyaluronidase. In the described mixture, strong adsorbing (binding) properties are exhibited by guar gum, which can adsorb the used active substances on its surface, in addition, the gum increases the viscosity of solutions, which may hinder the release of the active substances used at the place of application. The use of hyaluronidase, i.e. an enzyme with depolymerizing properties, which is also one of the two main allergens of bee venom, is also controversial. After administration of hyaluronidase, more serious side effects may occur in the form of hypotension, convulsions, dizziness, chills, nausea or vomiting. Severe allergic reactions, including anaphylactic shock and death, also occur. The degradation of hyaluronic acid by hyaluronidase causes an increase in the permeability of connective tissue and a decrease in the viscosity of body fluids, which facilitates the spread of microorganisms, toxins. As a result, further complications may occur. The existing solutions rely on the use of aqueous solutions of tetracaine hydrochloride and lidocaine introduced into hydrophilic bases (emulsions, creams, gels-Pliaglis preparation) or water-insoluble forms (lidocaine and tetracaine bases) in lipophilic bases (petrolatum).

Therefore, what is sought is a lipophilic base ensuring the introduction or emulsification of both water-soluble anesthetic active substances and at the same time increasing their bioavailability, thanks to which it is possible to reduce the doses of these substances while increasing their action and, additionally, to obtain a semi-solid mass of high homogeneity and uniformity with low level of contamination, and the composition containing it. Unexpectedly, the said problem was solved by the present invention

BRIEF SUMMARY OF THE INVENTION

The first subject of the invention is a pharmaceutical base for anesthetic active substances characterized in that it contains a strongly solvating aprotic solvent from the group of sulfoxides, preferably dimethyl sulfoxide, in an amount of from 0.25% to 15% by weight of the drug, carbonic acid amide, preferably urea, in an amount of 1% to 5% by weight of the drug, and animal fat with unsaturated fatty acids content up to about 55%, preferably Adeps suilus, an organic chemical compound from the group of dihydric alcohols, preferably 1,2-propylene glycol, from 5% to 15% by weight of the drug, organic chemical compound from the group of aliphatic alcohols, preferably isopropanol, from 0.05% to 1.5% by weight of the drug, organic chemical compound from the group of omega-9 monounsaturated fatty acids, preferably oleic acid, from 2% to 10% by weight of the drug.

The second object of the invention is a pharmaceutical composition, characterized in that it comprises the base as defined in the first object of the invention, and active substances, wherein the weight ratio of excipients:anhydrous pharmaceutical ointment base to pork lard is 1:2 to 2:1 and the weight ratio of the alcohol mixture, isopropyl and glycol, ranges from 1:5 to 1:15, and it contains dimethyl sulfoxide in the range of 0.25% to 15% by weight of the composition. Equally preferably, the composition is characterized in that it has a pH in the range 8.5 to 10.5. In another preferred embodiment of the invention, the composition contains propylene glycol in the range of 5% to 15% by weight of the composition. In a further preferred embodiment of the invention, the composition contains isopropyl alcohol in the range of f 0.5% to 1.5% by weight of the composition. In another preferred embodiment of the invention, the composition contains urea in the range of 1% to 5% by weight of the composition. Equally preferably, the composition according to the invention contains oleic acid in the range of 2% to 10% by weight of the composition. Most preferably, the composition according to the invention is characterized in that the active ingredient is at least one selected from the group consisting of lidocaine, tetracaine, prilocaine, benzocaine, bupivacaine, mepivacaine, preferably lidocaine and tetracaine or pharmaceutically acceptable salts thereof.

Lidocaine and tetracaine are released into the epidermal and dermal layers of the skin with the accumulation of lidocaine and tetracaine in the area of pain receptors and nerve endings in the skin. Both lidocaine and tetracaine block the sodium ion flow channels necessary to initiate and transfer impulses, leading to local anesthesia. The degree of anesthesia depends on the duration of the drug application.

Systemic exposure to the active substances depends on the dose, application time, skin thickness (which varies in different parts of the body) and skin condition. Absorbed doses of lidocaine and tetracaine are low after proper use. The extent to which lidocaine and tetracaine are metabolized in the skin is unknown. Lidocaine and its metabolites are excreted by the kidneys. The mean elimination half-life of lidocaine in plasma 30 min after topical administration of 9 g (200 cm2) of preparation is up to 12.1 h, indicating that a portion of the drug with prolonged action is placed in the skin tissue, from which the drug is then released into the circulatory system. The elimination half-life and clearance of tetracaine in humans has not been established, however, hydrolysis in plasma is rapid.

It can also be used for local anesthesia of the genital mucosa, e.g. prior to surface infiltration anesthesia or surface surgery and local anesthesia of leg ulcers to facilitate mechanical debridement of the wound, only in adults.

DETAILED DESCRIPTION OF THE INVENTION

Examples of active ingredients used in the invention:
Lidocaine (Latin Lidocainum; lignocaine, xylocaine)—an organic chemical compound, a derivative of acetanilide. Used as a local anesthetic.

Lidocaine—Physical Description
  White crystalline powder
  Identification of A, C according to EP
  Melting point 66-70° C. (identification test B)
  Solubility (5% in ethanol). Clear, colorless solution
  Impurity A≤0.01% (2,6-dimethylaniline)
  Each individual impurity≤0.1%
  Total impurities≤0.5%
  Chlorides≤35 ppm
  Sulphates≤0.1%
  Sulphated ash≤0.1%
  Water≤1.0%
  Purity 99.0-101.0% (by anhydrous basis) Complies with EP Lidocaine Hydrochloride—Physical Description
  White or almost white crystalline powder, very well soluble in water, freely soluble in ethanol
  Identification Melting point: 74-79° C., IR
  Reaction with alcohol solution of potassium hydroxide
  Reaction with chlorides
  The appearance of the solution. 5% solution: clear and colorless pH 4.0-5.5
  Related substances Impurity A: ≤0.01%
  Any unspecified impurity: ≤0.10%
  Total impurities: ≤0.5%
  Heavy metals≤5 ppm
  Sulphated ash≤0.1%
  Water (KF) 5.5-7.0%
  Residual Solvents Acetone: ≤5000 ppm, Toluene: ≤890 ppm
  Purity 99.0-101.0% (by anhydrous basis)
  Complies with EP It is usually administered transdermally in the form of an aerosol or gel. In dentistry, it is most often used in the form of a two-percent solution of lidocaine hydrochloride in ampoules (in pure form or with the addition of adrenaline or noradrenaline). Both free base lidocaine and the hydrochloride are used in medicine.

Mechanism of Action:

An amide derivative with a local anesthetic effect and anti-arrhythmic drug from Ib group according to Vaughan Williams classification. It stabilizes cell membranes by inhibiting the rapid flow of sodium ions and preventing cell depolarization under the influence of an incoming stimulus. Lidocaine shortens the duration of the action potential and the refractory period. This action affects the Purkinje fibers and the muscle membrane of the ventricles (not the atria). Reduces heart automatism. The effect is enhanced in the presence of high heart rate, hypokalemia, acidosis, in ischemic tissue. When administered as a plaster, lidocaine continuously penetrates the skin and has a local analgesic effect, which results from the stabilization of neuronal cell membranes. Clinical studies have demonstrated the analgesic efficacy of lidocaine administered in the perioperative period and improved intestinal motor function after radical prostatectomy, and in abdominal surgery (laparoscopic and laparotomy), a lower percentage of atony and postoperative intestinal obstruction, nausea and vomiting, which translated into shorter hospital stay. The perioperative use of lidocaine reduces the need for opioids. In addition to its analgesic effect, lidocaine used i.v. inhibits the inflammatory response induced by surgery. It is believed that the result of its use in the postoperative period is a decrease in plasma concentrations of, among others, IL-6, IL-8, C3a, IL-1ra, CD11b, L- and P-selectin. Moreover, the analgesic efficacy of lidocaine may be significantly greater in visceral pain than in somatic pain.

Pharmacokinetics

It is absorbed from the gastrointestinal tract in 30-40% and is immediately hydrolysed in the liver ("first pass" effect). After penetrating the blood, it quickly reaches the tissues and its serum concentration decreases rapidly. The first phase of distribution lasts 30 minutes, t1/2 of the drug in this period is 10 minutes. After i.v. administration, the anti-arrhythmic effect occurs already after 45-90 s, and after endotracheal administration it occurs after 10-15 s, reaching a peak after 1-2 min. The anti-arrhythmic effect lasts 10-20 minutes in the first case, and 30-50 minutes in the second. Under infiltration anesthesia, the drug starts working after 30-60 seconds, the effect lasts for 30-60 minutes. After epidural administration, the effect appears after 5-15 minutes and lasts up to 4 hours. The addition of epinephrine (5 µg/ml) extends the effect by 50%. After topical administration, lidocaine is easily absorbed from the mucosa and damaged skin, while it is poorly absorbed from unchanged skin. The rate of absorption and the dose absorbed after such administration depend on the dose used, the vascularity, surface area and condition of the injection site, as well as the time the injection site was exposed to the drug. The effect after administration in the form of an aerosol appears after 1 min and lasts 5-6 min, while after administration in the form of a gel it appears after 2-3 min and lasts 30-60 min. 70% is bound to plasma proteins, they are acute phase proteins, the amount of which increases under stress. It should be taken into account that in such conditions (e.g. in recent myocardial infarction) the amount of lidocaine binding proteins is higher, which increases t1/2 of the drug up to 2-fold. In the second phase of distribution, the drug is distributed more slowly in the body, and its immediate effectiveness weakens. Therefore, in the treatment of arrhythmias, it is recommended to administer additional 2 or 3 half-size doses, 10 minutes apart after the first. t1/2 in this phase is 1.5-2 h. 90% of lidocaine is metabolized by microsomal liver enzymes to inactive and active metabolites. It is excreted by the kidneys in 10% unchanged, the rest in the form of metabolites.

Tetracaine (Latin tetracainum)—a multifunctional organic chemical compound, a derivative of p-aminobenzoic acid. Used under local and intrathecal anesthesia.

Tetracaine—Physical Description

White, almost white or light yellow crystalline powder

Solubility (1% in ethanol). Clear, colorless to slightly yellow solution

Melting point 41.0-46.0° C.

Residue on ignition≤0.1%

Loss on drying≤2.0%

Purity 98.0-102.0% (dried base)

Tetracaine Hydrochloride—Physical Description

Appearance Solid, white

No smell pH approx. 4-6

Melting point/freezing point 148° C.

Initial boiling point and boiling range no data g) Flash point >100° C.

Evaporation speed no data

Flammability (solid, gas) no data available

Relative density 0.416 kg/1

Water solubility 150 g/l

Partition coefficient: n-octanol/water not available

Decomposition temperature no data available

Viscosity no data available

The Mechanism of Action

Tetracaine induces local anesthesia by reversible blockade of nerve conduction, reducing or completely preventing temporary increases in sodium ion permeability of the cell membrane, possibly through competitive binding to the calcium ion binding site.

Use of the Invention

Surface anesthesia of the skin due to needle insertion and in the case of superficial surgical procedures on unchanged, intact skin in adults, local anesthesia of the skin before dermatological procedures on intact skin in adults, surface anesthesia of the skin associated with the insertion of a needle into unchanged, intact skin in children over 3 years of age, pain and itching in the area of the anus, inflammation of the rectal mucosa, thrombosis of the hemorrhoids, adjuvant treatment after surgical procedures of perianal fistulas and hemorrhoids.

Tetracaine is included in the WHO Model Lists of Essential Medicines (2015).

Tetracaine is authorized in Poland (2018).

Auxiliary Substances:

Anhydrous pharmaceutical ointment base with the following composition:

Alcohol cetylicus_et stearylicus 0.5 part (cetostearyl alcohol)

Alcoholes adipis lanae 6.0 parts (lanolin alcohols)

Vaselinum album 93.5 parts (white vaseline) or alternatively

Alcohol cetylicus 3.0 parts (cetyl alcohol)

Cholesterolum 2 parts (Cholesterol)

Vaselinum album 95 parts (white Vaseline)—galenic preparation for external use, prepared according to the pharmacopoeial recipe. In Poland, the first detailed monograph of this ointment appeared in the Polish Pharmacopoeia supplement FP IX (2013). Currently (2018) it is in the Polish Pharmacopoeia XI. It is classified as an anhydrous pharmaceutical ointment base with absorptive and lipophilic properties. The water content of the above-mentioned base is high; for pharmacopoeial preparations, it may not be less than 300. Used in the pharmaceutical and cosmetic industries and in pharmacy formulas as the basis for anhydrous ointments, emulsion ointments and creams. It can also be used alone per se as a moisturizing neutral ointment with a protective effect.

Pork lard (Latin Adeps suillus)—The main component of lard (over 99%) is fats, the majority of which contain unsaturated acids (over 55% by weight). Contrary to popular belief, the amount of saturated fatty acids does not exceed 40%. Pork lard has been used in pharmacy as a pharmaceutical raw material in a pharmacy recipe under the Latin name Adeps suillus or Axungia Porci. Lard used as a base for the production of therapeutic ointments must meet the requirements of pharmaceutical quality specified in the current monograph of the Polish Pharmacopoeia.

Dimethyl sulfoxide, DMSO, (CH3)2SO—an organic chemical compound from the group of sulfoxides. It is used as an analytical and chemical reagent and solvent in spectroscopy and chromatography, among others. It is also of limited use as an anti-inflammatory and analgesic drug and as a cryoprotectant. Due to its polarity, DMSO is miscible with water and can be used as a solvent for other polar compounds, for example sodium chloride (NaCl). DMSO belongs to the class of strongly solvating aprotic solvents.

Propylene glycol (propane-1,2-diol)—an organic chemical compound from the group of dihydric alcohols, i.e. diols. At room temperature, it is a colorless, odorless, oily liquid with a sweetish taste and high viscosity. It is widely used in industry and medicine. Unlike ethylene glycol, propylene glycol is not toxic. Propylene glycol is a hygroscopic substance. It is soluble, among others, in water, acetone and chloroform. The molecule contains an asymmetric carbon atom and can exist in the form of two enantiomers. Except special applications, it is a racemic mixture. Individual enantiomers may be obtained by hydrating one of the propylene oxide enantiomers. Propylene glycol is used in pharmacy as a base, i.e. a fluid which itself has no significant effect on the body, but in which the active ingredient of the drug can be distributed. This applies primarily to medicinal substances that do not dissolve in water, but can be dissolved in propylene glycol. Thus, propylene glycol can be used in the form of an oral preparation as well as a cream. In the latter case, it is applied topically to the skin.

Isopropanol (propan-2-ol, isopropyl alcohol)—an organic chemical compound from the group of aliphatic alcohols. Is the simplest secondary alcohol. It has one substituent isomer, propan-1-ol. Used as a mild organic solvent, as well as a solvent and carrier for HPLC, and in chemical synthesis as a reagent for introducing the isopropyl and isopropoxy groups.

Urea (carbamide, E927b), $CO(NH2)2$—an organic chemical compound, carbonic acid diamide. It forms colorless crystals in the form of long and colorless needles, odorless, with a melting point of approx. 133° C., and decomposes with further heating before reaching the boiling point. It is hygroscopic and easily soluble in water.

Oleic acid (Latin acidum oleicum, from oleum-oil)—an organic chemical compound from the group of omega-9 monounsaturated fatty acids. It is a cis-isomer of elaidic acid. Naturally, this acid is found in fats (it is the main ingredient in olive oil and fish oil) from which it is extracted.

The present invention aims to overcome the disadvantages of the prior art and provide an ointment with a broader spectrum of indications while reducing the doses of anesthetics used, which is associated with a reduction in side effects. In this regard, the invention provides an ointment that leads to an anesthetic effect when applied topically.

The inventors have found that the ointment is effective in causing local anesthesia of the skin, which lasts for a certain period of use depending on the composition of the base.

Example 1

The anesthetic ointments and cosmetic creams base containing pork lard and anhydrous pharmaceutical ointment base consisting of isopropyl alcohol and 1,2-propylene glycol, oleic acid and urea, and a pH adjuster-20% sodium hydroxide solution.

The method for producing a medicated ointment and a cosmetic cream base consisted in melting and mixing the ingredients. 32.0 g of pork lard was added to 34.0 g of an anhydrous pharmaceutical ointment base with constant stirring. Then, the solids were introduced into 16.0 g of mixture obtained by mixing isopropyl alcohol-1.1 g, 1,2-propylene glycol-10.1 g, oleic acid-4.8 g, heated to 60 deg. C, in the following order:
  a) 2.0 g of urea and it is stirred at elevated temperature until a liquid, clear mixture is obtained.
  b) a prescription amount of lidocaine hydrochloride (3.8 g) and tetracaine hydrochloride (3.8 g) and it is stirred at an elevated temperature until a liquid, clear mixture is obtained.

In the next stage, it is cooled to 40 deg. C with continuous stirring, and then added to the base and mixed until a uniform consistency is obtained. 8 g of 20% sodium hydroxide solution is added to the ointment thus obtained to obtain an ointment with a pH of 8.5. Mixing is carried out for 10 min±5 min until a homogeneous ointment is obtained. The formulation thus prepared containing 3.8% of lidocaine HCl and 3.8% of tetracaine HCl was tested for pharmaceutical availability in an in vitro model using a paddle device for drug substance release. The study was conducted for 10 in hours six parallel chambers. The concentration of active substances was tested using a UV-VIS spectrophotometer. Samples for testing were taken at intervals of 5 minutes, 15 minutes, 30 minutes, 1 h, 2 h, 3 h, 4 h, 5 h, 6 h, 7 h, 10 h. Commercial hydrogel formulations containing lidocaine HCl and tetracaine HCl at a concentration of 7% were used as reference. During the study, it was shown that the average level of active substances released from the formulation described in the exemplary embodiment was on average 34% higher for lidocaine HCl and 28% higher for tetracaine HCl, at each measurement point, compared to a hydrogel containing lidocaine and tetracaine at a concentration of 7%.

Example 2

The anesthetic ointment and cosmetic creams base containing pork lard and anhydrous pharmaceutical ointment base consisting of pork lard and water-free pharmaceutical ointment base, isopropyl alcohol and 1,2-propylene glycol, oleic acid and urea, and a pH adjuster-20% hydroxide solution.

A method for producing a medicated ointment and a cosmetic cream base consisting in melting and mixing the ingredients, characterized in that 32.0 g of an anhydrous pharmaceutical ointment base is added to 32.0 g of pork lard with constant stirring. Then, the solids were introduced into 16.0 g of the mixture obtained by mixing isopropyl alcohol-0.9 g, 1,2-propylene glycol-10.1 g, oleic acid-4.8 g, heated to 60 deg. C, in the following order:
  a) 2.0 g of urea and it is stirred at elevated temperature until a liquid, clear mixture is obtained.
  b) a prescription amount of lidocaine hydrochloride (4.1 g) and tetracaine hydrochloride (4.1 g) and it is stirred at an elevated temperature until a liquid, clear mixture is obtained.

In the next stage, it is cooled to 40 deg. C with continuous stirring, and then added to the base and mixed until a uniform consistency is obtained.

10 g of a 20% sodium hydroxide solution is added to the ointment thus obtained, to obtain an ointment with a pH of 10.47. Mixing is carried out for 10 min±5 min until a homogeneous ointment is obtained.

The formulation thus prepared containing lidocaine HCl and tetracaine HCl at a concentration of 4.1% was subjected to an in vitro pharmaceutical availability study using a paddle device for drug substance release. The study was conducted for 10 hours in six parallel chambers. The concentration of active substances was tested using a UV-VIS spectrophotometer. Samples for testing were taken at intervals of 5 minutes, 15 minutes, 30 minutes. 1 h, 2 h, 3 h, 4 h, 5 h, 6 h, 7 h, 10 h. Commercially available preparations in the form of a hydrogel containing lidocaine HCl and tetracaine HCl in a concentration of 7% were used as a reference. During the study, it was shown that the average level of active substances released from the formulation described in the embodiment was on average 26% higher for lidocaine HCl and 22.4% higher for tetracaine HCl at each measurement point compared to hydrogel containing lidocaine and tetracaine at a concentration of 7%.

3. Third Embodiment

The anesthetic ointment and cosmetic creams base containing pork lard and anhydrous pharmaceutical ointment base characterized in that it consists of pork lard and anhydrous pharmaceutical ointment base, isopropyl alcohol and 1,2-propylene glycol, oleic acid and urea, and a pH adjuster-20% hydroxide solution.

A method for producing a medicated ointment and a cosmetic cream base consisting in melting and mixing the ingredients, characterized in that 36.0 g of an anhydrous pharmaceutical ointment base is added to 18.0 g of pork lard with constant stirring.

Then, the solids are introduced into 16.0 g of the mixture obtained by mixing isopropyl alcohol-1.0 g, 1,2-propylene glycol-10.0 g, oleic acid-5.0 g, heated to 60 deg. C, in the following order:
  a) 2.0 g of urea and it is stirred at elevated temperature until a liquid, clear mixture is obtained.
  b) a prescription amount of lidocaine hydrochloride (3.9 g) and tetracaine hydrochloride (4.1 g) and it is stirred at an elevated temperature until a liquid, clear mixture is obtained.

In the next stage, it is cooled to 40 deg. C with continuous stirring, and then added to the base and mixed until a uniform consistency is obtained.

10 g of a 20% sodium hydroxide solution is added to the ointment thus obtained, to obtain an ointment with a pH of 10.47. Mixing is carried out for 10 min±5 min until a homogeneous ointment is obtained.

The formulation thus prepared containing lidocaine HCl (3.9%) and tetracaine HCl (4.1%) was subjected to an in vitro pharmaceutical availability study using a paddle device for drug substance release. The study was conducted for 10 hours in six parallel chambers. The concentration of active substances was tested using a UV-VIS spectrophotometer. Samples for testing were taken at intervals of 5 minutes, 15 minutes, 30 minutes, 1 h, 2 h, 3 h, 4 h, 5 h, 6 h, 7 h, 10 h. Commercially available preparations in the form of a hydrogel containing lidocaine HCl and tetracaine HCl in a concentration of 7% were used as a reference. During the study, it was shown that the average level of active substances released from the formulation described in the embodiment was on average 29.5% higher for lidocaine HCl and 19.6% higher for tetracaine HCl at each measurement point compared to hydrogel containing lidocaine and tetracaine at a concentration of 7%.

4. Fourth Embodiment

The anesthetic ointment and cosmetic creams base containing pork lard and anhydrous pharmaceutical ointment base, characterized in that it consists of pork lard and anhydrous pharmaceutical ointment base, isopropyl alcohol and 1,2-propylene glycol, oleic acid and urea, and a pH adjuster-20% hydroxide solution.

A method for producing medicated ointment and a cosmetic cream base consisting in melting and mixing the ingredients, characterized in that 18.0 g of an anhydrous pharmaceutical ointment base is added to 36.0 g of pork lard with constant stirring.

Then, the solids are introduced into 16.0 g of the mixture obtained by mixing isopropyl alcohol-0.8 g, 1,2-propylene glycol-10.2 g, oleic acid-5.1 g, heated to 60 deg. C, in the following order:
  a) 1.9 g of urea and it is stirred at elevated temperature until a liquid, clear mixture is obtained.
  b) a prescription amount of lidocaine hydrochloride (4.1 g) and tetracaine hydrochloride (3.9 g) and it is stirred at an elevated temperature until a liquid, clear mixture is obtained.

In the next stage, it is cooled to 40 deg. C with continuous stirring, and then added to the base and mixed until a uniform consistency is obtained.

10 g of a 20% sodium hydroxide solution is added to the ointment thus obtained, to obtain an ointment with a pH of 10.47. Mixing is carried out for 10 min±5 min until a homogeneous ointment is obtained.

The formulation thus prepared containing lidocaine HCl (4.1%) and tetracaine HCl (3.9%) was subjected to an in vitro pharmaceutical availability study using a paddle device for drug substance release. The study was conducted for 10 hours in six parallel chambers. The concentration of active substances was tested using a UV-VIS spectrophotometer. Samples for testing were taken at intervals of 5 minutes, 15 minutes, 30 minutes, 1 h, 2 h, 3 h, 4 h, 5 h, 6 h, 7 h, 10 h. Commercially available preparations in the form of a hydrogel containing lidocaine HCl and tetracaine HCl in a concentration of 7% were used as a reference. During the study, it was shown that the average level of active substances released from the formulation described in the embodiment was on average 38.2% higher for lidocaine HCl and 32% higher for tetracaine HCl at each measurement point compared to hydrogel containing lidocaine and tetracaine at a concentration of 7%.

5. Fifth Embodiment

The anesthetic ointment and cosmetic creams base containing pork lard and anhydrous pharmaceutical ointment base, characterized in that it consists of pork lard and anhydrous pharmaceutical ointment base, isopropyl alcohol and 1,2-propylene glycol, oleic acid and urea, and a pH adjuster-20% hydroxide solution.

A method for producing medicated ointment and a cosmetic cream base consisting in melting and mixing the ingredients, characterized in that 32.0 g of an anhydrous pharmaceutical ointment base is added to 37.0 g of pork lard with constant stirring.

Then, the solids are introduced into 11.0 g of the mixture obtained by mixing isopropyl alcohol-1.0 g, 1,2-propylene glycol-5.0 g, oleic acid-5.0 g, heated to 60 deg. C, in the following order:
  a) 2.0 g of urea and it is stirred at elevated temperature until a liquid, clear mixture is obtained.
  b) a prescription amount of lidocaine hydrochloride (4 g) and tetracaine hydrochloride (4 g) and it is stirred at an elevated temperature until liquid, clear mixture is obtained.

In the next stage, it is cooled to 40 deg. C with continuous stirring, and then added to the base and mixed until a uniform consistency is obtained.

10 g of a 20% sodium hydroxide solution is added to the ointment thus obtained, to obtain an ointment with a pH of 10.47. Mixing is carried out for 10 min±5 min until a homogeneous ointment is obtained.

The formulation thus prepared containing lidocaine HCl and tetracaine HCl at a concentration of 4% was subjected to an in vitro pharmaceutical availability study using a paddle device for drug substance release. The study was conducted for 10 hours in six parallel chambers. The concentration of active substances was tested using a UV-VIS spectrophotometer. Samples for testing were taken at intervals of 5 minutes, 15 minutes, 30 minutes, 1 h, 2 h, 3 h, 4 h, 5 h, 6 h, 7 h, 10 h. Commercially available preparations in the form of a hydrogel containing lidocaine HCl and tetracaine HCl in a concentration of 7% were used as a reference. During the study, it was shown that the average level of active substances released from the formulation described in the embodiment was on average 31% higher for lidocaine HCl and 29.3% higher for tetracaine HCl at each measurement point compared to hydrogel containing lidocaine and tetracaine at a concentration of 7%.

6. Sixth Embodiment

The anesthetic ointment and cosmetic creams base containing pork lard and anhydrous pharmaceutical ointment base, characterized in that it consists of pork lard and anhydrous pharmaceutical ointment base, isopropyl alcohol and 1,2-propylene glycol, oleic acid and urea, and a pH adjuster-20% hydroxide solution solution.

A method for producing medicated ointment and a cosmetic cream base consisting in melting and mixing the ingredients, characterized in that 32.0 g of an anhydrous pharmaceutical ointment base is added to 27.0 g of pork lard with constant stirring.

Then, the solids are introduced into 21.0 g of the mixture obtained by mixing isopropyl alcohol-1.0 g, 1,2-propylene glycol-15.0 g, oleic acid-5.0 g, heated to 60 deg. C, in the following order:
  a) 2.0 g of urea and it is stirred at elevated temperature until a liquid, clear mixture is obtained.
  b) a prescription amount of lidocaine hydrochloride (4 g) and tetracaine hydrochloride (4 g) and it is stirred at an elevated temperature until a liquid, clear mixture is obtained.

In the next stage, it is cooled to 40 deg. C with continuous stirring, and then added to the base and mixed until a uniform consistency is obtained.

10 g of a 20% sodium hydroxide solution is added to the ointment thus obtained, to obtain an ointment with a pH of 10.47. Mixing is carried out for 10 min±5 min until a homogeneous ointment is obtained.

The formulation thus prepared containing lidocaine HCl and tetracaine HCl at a concentration of 4% was subjected to an in vitro pharmaceutical availability study using a paddle device for drug substance release. The study was conducted for 10 hours in six parallel chambers. The concentration of active substances was tested using a UV-VIS spectrophotometer. Samples for testing were taken at intervals of 5 minutes, 15 minutes, 30 minutes, 1 h, 2 h, 3 h, 4 h, 5 h, 6 h, 7 h, 10 h. Commercially available preparations in the form of a hydrogel containing lidocaine HCl and tetracaine HCl in a concentration of 7% were used as a reference. During the study, it was shown that the average level of active substances released from the formulation described in the embodiment was on average 26.4% higher for lidocaine HCl and 27.6% higher for tetracaine HCl at each measurement point compared to hydrogel containing lidocaine and tetracaine at a concentration of 7%.

7. Seventh Embodiment

The anesthetic ointment and cosmetic creams base containing pork lard and anhydrous pharmaceutical ointment base, characterized in that it consists of pork lard and anhydrous pharmaceutical ointment base, DMSO, isopropyl alcohol and 1,2-propylene glycol, oleic acid and urea, and a pH adjuster-20% hydroxide solution. A method for producing medicated ointment and a cosmetic cream base consisting in melting and mixing the ingredients, characterized in that 32.0 g of an anhydrous pharmaceutical ointment base is added to 31.75 g of pork lard with constant stirring.

Then, the solids are introduced into 16.25 g of the mixture obtained by mixing isopropyl alcohol-1.2 g, 1,2-propylene glycol-9.8.0 g, DMSO-0.25 g, oleic acid-5.0 g, heated to 60 deg. C, in the following order:
  a) 2.0 g of urea and it is stirred at elevated temperature until a liquid, clear mixture is obtained.
  b) a prescription amount of lidocaine hydrochloride (4 g) and tetracaine hydrochloride (4 g) and it is stirred at an elevated temperature until a liquid, clear mixture is obtained.

In the next stage, it is cooled to 40 deg. C with continuous stirring, and then added to the base and mixed until a uniform consistency is obtained.

10 g of a 20% sodium hydroxide solution is added to the ointment thus obtained, to obtain an ointment with a pH of 10.47. Mixing is carried out for 10 min±5 min until a homogeneous ointment is obtained.

The formulation thus prepared containing lidocaine HCl and tetracaine HCl at a concentration of 4% was subjected to an in vitro pharmaceutical availability study using a paddle device for drug substance release. The study was conducted for 10 hours in six parallel chambers. The concentration of active substances was tested using a UV-VIS spectrophotometer. Samples for testing were taken at intervals of 5 minutes, 15 minutes, 30 minutes, 1 h, 2 h, 3 h, 4 h, 5 h, 6 h, 7 h, 10 h. Commercially available preparations in the form of a hydrogel containing lidocaine HCl and tetracaine HCl in a concentration of 7% were used as a reference. During the study, it was shown that the average level of active substances released from the formulation described in the embodiment was on average 31.8% higher for lidocaine HCl and 22.3% higher for tetracaine HCl at each measurement point compared to hydrogel containing lidocaine and tetracaine at a concentration of 7%.

8. Eighth Embodiment

The anesthetic ointment and cosmetic creams base containing pork lard and anhydrous pharmaceutical ointment base, characterized in that it consists of pork lard and anhydrous pharmaceutical ointment base, DMSO, isopropyl alcohol and 1,2-propylene glycol, oleic acid and urea, and a pH adjuster-20% hydroxide solution. A method for producing medicated ointment and a cosmetic cream base consisting in melting and mixing the ingredients, characterized in that 32.0 g of an anhydrous pharmaceutical ointment base is added to 18.0 g of pork lard with constant stirring.

Then, the solids are introduced into 30.0 g of the mixture obtained by mixing isopropyl alcohol-0.5 g, 1,2-propylene glycol-10.5 g, DMSO-15 g, oleic acid-4.0 g, heated to 60 deg. C, in the following order:
  a) 2.0 g of urea and it is stirred at elevated temperature until a liquid, clear mixture is obtained.
  b) a prescription amount of lidocaine hydrochloride (4 g) and tetracaine hydrochloride (4 g) and it is stirred at an elevated temperature until a liquid, clear mixture is obtained.

In the next stage, it is cooled to 40 deg. C with continuous stirring, and then added to the base and mixed until a uniform consistency is obtained.

10 g of a 20% sodium hydroxide solution is added to the ointment thus obtained, to obtain an ointment with a pH of 10.47. Mixing is carried out for 10 min±5 min until a homogeneous ointment is obtained.

The formulation thus prepared containing lidocaine HCl and tetracaine HCl at a concentration of 4% was subjected to an in vitro pharmaceutical availability study using a paddle device for drug substance release. The study was conducted for 10 hours in six parallel chambers. The concentration of active substances was tested using a UV-VIS spectrophotometer. Samples for testing were taken at intervals of 5 minutes, 15 minutes, 30 minutes, 1 h, 2 h, 3 h, 4 h, 5 h, 6 h, 7 h, 10 h. Commercially available preparations in the form of a hydrogel containing lidocaine HCl and tetracaine HCl in a concentration of 7% were used as a reference. During the study, it was shown that the average level of active substances released from the formulation described in the embodiment was on average 21.5% higher for lidocaine HCl and 20.4% higher for tetracaine HCl at each measurement point compared to hydrogel containing lidocaine and tetracaine at a concentration of 7%.

9. Ninth Embodiment

The anesthetic ointment and cosmetic creams base containing pork lard and anhydrous pharmaceutical ointment base, characterized in that it consists of pork lard and anhydrous pharmaceutical ointment base, DMSO, isopropyl alcohol and 1,2-propylene glycol, oleic acid and urea, and a pH adjuster-20% hydroxide solution. A method for producing medicated ointment and a cosmetic cream base consisting in melting and mixing the ingredients, characterized in that 33.75 g of an anhydrous pharmaceutical ointment base is added to 31.00 g of pork lard with constant stirring.

Then, the solids are introduced into 15.25 g of the mixture obtained by mixing isopropyl alcohol-0.5 g, 1,2-propylene glycol-9.5 g, DMSO-0.25 g, oleic acid-5.0 g, heated to 60 deg. C, in the following order:

a) 2.0 g of urea and it is stirred at elevated temperature until a liquid, clear mixture is obtained.

b) a prescription amount of lidocaine hydrochloride (4 g) and mepivacaine hydrochloride (4 g) and it is stirred at an elevated temperature until a liquid, clear mixture is obtained.

In the next stage, it is cooled to 40 deg. C with continuous stirring, and then added to the base and mixed until a uniform consistency is obtained.

10 g of a 20% sodium hydroxide solution is added to the ointment thus obtained, to obtain an ointment with a pH of 10.47. Mixing is carried out for 10 min±5 min until a homogeneous ointment is obtained.

The formulation thus prepared containing lidocaine HCl and mepivacaine HCl at a concentration of 4% was subjected to an in vitro pharmaceutical availability study using a paddle device for drug substance release. The study was conducted for 10 hours in six parallel chambers. The concentration of active substances was tested using a UV-VIS spectrophotometer. Samples for testing were taken at intervals of 5 minutes, 15 minutes, 30 minutes, 1 h, 2 h, 3 h, 4 h, 5 h, 6 h, 7 h, 10 h. Commercially available preparations in the form of a hydrogel containing lidocaine HCl and mepivacaine HCl at a concentration of 7% were used as a reference. During the study, it was shown that the average level of active substances released from the formulation described in the embodiment was on average 24.7% higher for lidocaine HCl and 25.2% higher for mepivacaine HCl at each measurement point compared to hydrogel containing lidocaine and mepivacaine at a concentration of 7%.

10. Tenth Embodiment

The anesthetic ointment and cosmetic creams base containing pork lard and anhydrous pharmaceutical ointment base, characterized in that it consists of pork lard and anhydrous pharmaceutical ointment base, DMSO, isopropyl alcohol and 1,2-propylene glycol, oleic acid and urea, and a pH adjuster-20% hydroxide solution. A method for producing medicated ointment and a cosmetic cream base consisting in melting mixing the ingredients, characterized in that 32.0 g of an anhydrous pharmaceutical ointment base is added to 31.25 g of pork lard with constant stirring.

Then, the solids are introduced into 16.75 g of the mixture obtained by mixing isopropyl alcohol-1.5 g, 1,2-propylene glycol-9.5 g, DMSO-0.25 g, oleic acid-5.0 g, heated to 60 deg. C, in the following order:

a) 2.0 g of urea and it is stirred at elevated temperature until a liquid, clear mixture is obtained.

b) a prescription amount of lidocaine hydrochloride (4 g) and benzocaine hydrochloride (4 g) and it is stirred at an elevated temperature until liquid, clear mixture is obtained.

In the next stage, it is cooled to 40 deg. C with continuous stirring, and then added to the base and mixed until a uniform consistency is obtained.

10 g of a 20% sodium hydroxide solution is added to the ointment thus obtained, to obtain an ointment with a pH of 10.47. Mixing is carried out for 10 min±5 min until a homogeneous ointment is obtained.

The formulation thus prepared containing lidocaine HCl and benzocaine HCl at a concentration of 4% was subjected to an in vitro pharmaceutical availability study using a paddle device for drug substance release. The study was conducted for 10 hours in six parallel chambers. The concentration of active substances was tested using a UV-VIS spectrophotometer. Samples for testing were taken at intervals of 5 minutes, 15 minutes, 30 minutes, 1 h, 2 h, 3 h, 4 h, 5 h, 6 h, 7 h, 10 h. The preparation in the form of a hydrogel containing lidocaine HCl and benzocaine HCl at a concentration of 7% was used as a reference. During the study, it was shown that the average level of active substances released from the formulation described in the embodiment was on average 18.7% higher for lidocaine HCl and 18.1% higher for benzocaine HCl at each measurement point compared to hydrogel containing lidocaine and benzocaine at a concentration of 7%.

11. Eleventh Embodiment

The anesthetic ointment and cosmetic creams base containing pork lard and anhydrous pharmaceutical ointment base, characterized in that it consists of pork lard and anhydrous pharmaceutical ointment base, DMSO, isopropyl alcohol and 1,2-propylene glycol, oleic acid and urea, and a pH adjuster-20% hydroxide solution solution.

A method for producing medicated ointment and a cosmetic cream base consisting in melting and mixing the ingredients, characterized in that 32.0 g of an anhydrous pharmaceutical ointment base is added to 31.75 g of pork lard with constant stirring.

Then, the solids are introduced into 13.25 g of the mixture obtained by mixing isopropyl alcohol-1.0 g, 1,2-propylene glycol-10.0 g, DMSO-0.25 g, oleic acid-2.0 g, heated to 60 deg. C, in the following order:

a) 5.0 g of urea and it is stirred at elevated temperature until a liquid, clear mixture is obtained.
b) a prescription amount of lidocaine hydrochloride (4 g) and prilocaine hydrochloride (4 g) and it is stirred at an elevated temperature until a liquid, clear mixture is obtained.

In the next stage, it is cooled to 40 deg. C with continuous stirring, and then added to the base and mixed until a uniform consistency is obtained.

10 g of a 20% sodium hydroxide solution is added to the ointment thus obtained, to obtain an ointment with a pH of 10.47. Mixing is carried out for 10 min±5 min until a homogeneous ointment is obtained.

The formulation thus prepared containing lidocaine HCl and prilocaine HCl at a concentration of 4% was subjected to an in vitro pharmaceutical availability study using a paddle device for drug substance release. The study was conducted for 10 hours in six parallel chambers. The concentration of active substances was tested using a UV-VIS spectrophotometer. Samples for testing were taken at intervals of 5 minutes, 15 minutes, 30 minutes, 1 h, 2 h, 3 h, 4 h, 5 h, 6 h, 7 h, 10 h. The preparation in the form of a hydrogel containing lidocaine HCl and prilocaine HCl at a concentration of 7% was used as a reference. During the study, it was shown that the average level of active substances released from the formulation described in the embodiment was on average 24.3% higher for lidocaine HCl and 17.9% higher for prilocaine HCl at each measurement point compared to hydrogel containing lidocaine and prilocaine at a concentration of 7%.

12. Twelfth Embodiment

The anesthetic ointment and cosmetic creams base containing pork lard and anhydrous pharmaceutical ointment base, characterized in that it consists of pork lard and anhydrous pharmaceutical ointment base, DMSO, isopropyl alcohol and 1,2-propylene glycol, oleic acid and urea, and a pH adjuster-20% hydroxide solution. A method for producing medicated ointment and a cosmetic cream base consisting in melting and mixing the ingredients, characterized in that 32.0 g of an anhydrous pharmaceutical ointment base is added to 27.75 g of pork lard with constant stirring.

Then, the solids are introduced into 21.25 g of the mixture obtained by mixing isopropyl alcohol-1.3 g, 1,2-propylene glycol-9.7 g, DMSO-0.25 g, oleic acid-10.0 g, heated to 60 deg. C, in the following order:
a) 1.0 g of urea and it is stirred at elevated temperature until a liquid, clear mixture is obtained.
b) a prescription amount of bupivacaine hydrochloride (4 g) and tetracaine hydrochloride (4 g) and it is stirred at an elevated temperature until a liquid, clear mixture is obtained.

In the next stage, it is cooled to 40 deg. C with continuous stirring, and then added to the base and mixed until a uniform consistency is obtained.

10 g of a 20% sodium hydroxide solution is added to the ointment thus obtained, to obtain an ointment with a pH of 10.47. Mixing is carried out for 10 min±5 min until a homogeneous ointment is obtained.

The formulation thus prepared containing lidocaine HCl and bupivacaine HCl at a concentration of 4% was subjected to an in vitro pharmaceutical availability study using a paddle device for drug substance release. The study was conducted for 10 hours in six parallel chambers. The concentration of active substances was tested using a UV-VIS spectrophotometer. Samples for testing were taken at intervals of 5 minutes, 15 minutes, 30 minutes, 1 h, 2 h, 3 h, 4 h, 5 h, 6 h, 7 h, 10 h. The preparation in the form of a hydrogel containing lidocaine HCl and bupivacaine HCl at a concentration of 7% was used as a reference. During the study, it was shown that the average level of active substances released from the formulation described in the embodiment was on average 25.4% higher for lidocaine HCl and 19.7% higher for bupivacaine HCl at each measurement point compared to hydrogel containing lidocaine and bupivacaine at a concentration of 7%. The base according to the invention is characterized by excellent properties, forming a very thin layer on the surface of the body, allowing easy and long-lasting penetration of medicinal substances into the body and their rapid absorption.

13. Thirteenth Embodiment

The anesthetic ointment and cosmetic creams base containing pork lard and anhydrous pharmaceutical ointment base, characterized in that it consists of pork lard and anhydrous pharmaceutical ointment base, DMSO, isopropyl alcohol and 1,2-propylene glycol, oleic acid and urea, and a pH adjuster-20% hydroxide solution solution.

A method for producing medicated ointment and a cosmetic cream base consisting in melting and mixing the ingredients, characterized in that 32.0 g of an anhydrous pharmaceutical ointment base is added to 31.5 g of pork lard with constant stirring.

Then, the solids are introduced into 16.5 g of the mixture obtained by mixing isopropyl alcohol-1.0 g, 1,2-propylene glycol-10.0 g, DMSO-0.5 g, oleic acid-5.0 g, heated to 60 deg. C, in the following order:
a) 2.0 g of urea and it is stirred at elevated temperature until a liquid, clear mixture is obtained.
b) a prescription amount of lidocaine hydrochloride (4 g) and tetracaine hydrochloride (4 g) and it is stirred at an elevated temperature until a liquid, clear mixture is obtained.

In the next stage, it is cooled to 40 deg. C with continuous stirring, and then added to the base and mixed until a uniform consistency is obtained.

10 g of a 20% sodium hydroxide solution is added to the ointment thus obtained, to obtain an ointment with a pH of 9.8. Mixing is carried out for 10 min±5 min until a homogeneous ointment is obtained.

The formulation thus prepared containing lidocaine HCl and tetracaine HCl at a concentration of 4% was tested for the pharmacokinetic profile in an in vivo model in cooperation with Charles River Laboratories Den Bosch BV. The aim of the study was to investigate the pharmacokinetics and bioavailability of intravenous and topical administration of lidocaine hydrochloride and tetracaine hydrochloride to laboratory animals (Goetingen mini-pigs).

The research used:

TEXT TABLE 1

Experimental Design

| Period[b] | Test Item Id. | Dose Level (mg/kg/test item) | Dose Volume[a] (mL/kg) | Dose Concentration (mg/mL) | Dose Route |
|---|---|---|---|---|---|
| 1 | Lidocaine (HCl) and Tetracaine (HCl) | 1[d] | 0.5 | 2 | Intravenous |

| Period[b] | Test Item Id. | Dose Concentration of API (%/test item) | Treatment Area (cm²) | Dose Amount[c] | Dose Route |
|---|---|---|---|---|---|
| 2 | Reference product available on the market (Reference product) | 7 | 100 | 10 g / 100 cm² | Topical |
| 3 | Formulation 13 | 4 | 100 | 10 g / 100 cm² | |

Id. = identification.
[a]Based on the most recent body weight measurement;
[b]There was a wash-out period of one week between Periods 1 and 2 and of two weeks between Periods 2 and 3;
[c]Animals were treated for 60 minutes;

Following intravenous administration of lidocaine HCl and tetrazine HCl (period 1), 2 (out of 3) dosed animals showed clinical signs such as slight somnolence, muscle strain and ventro-lateral sleep and blinking, moderate unco-ordinated movements and slight gait disturbance. After topical administration of the reference product (market product containing 7% lidocaine and tetracaine) and Formulation 13, clinical signs such as mild to moderate erythema and saccharide form were found in all animals.

Samples of biological material were collected according to the following scheme:

| | Bioanalytical Sample Collection Schedule | | | | | | | | |
|---|---|---|---|---|---|---|---|---|---|
| | Time Postdose (Period 1) and Time after Start of Application (Periods 2 and 3) | | | | | | | | |
| Period Numbers | 5 min (0.083 h) | 15 min (0.25 h) | 30 min (0.5 h) | 1 h | 2 h | 4 h | 8 h | 12 h | 24 h |
| 1 | — | — | X | X | X | X | X | X | X |
| 2 | | X | X | X | X | X | X | X | X |
| 3 | | X | X | X | X | X | X | X | X |

Intravenous administration at a dose of 1 mg/kg showed that tetracaine is a highly purified and highly dispersed compound. After topical administration of 10 g/animal, tmax was 1 to 8 hours for the comparative product containing 7% lidocaine and tetracaine and 2 to 8 hours for Formulation 13 (4% lidocaine and tetracaine) and the mean absolute bioavailability of tetracaine for topical use was 1.26% for the comparative product (7% lidocaine and tetracaine) and 3.34% for Formulation 13 (4% lidocaine and tetracaine).

Intravenous administration at a dose of 1 mg/kg showed that lidocaine is moderately purified and highly dispersed compound. After topical administration of 10 g/animal, tmax ranged from 2 to 4 hours for the reference product containing 7% lidocaine and tetracaine and from 2 to 8 hours for Formulation 13 (4% lidocaine and tetracaine), and the mean absolute bioavailability of lidocaine under local administration conditions was 1.41% for the reference product containing 7% lidocaine and tetracaine and 1.98% for Formulation 13 (4% lidocaine and tetracaine).

Figure 1:
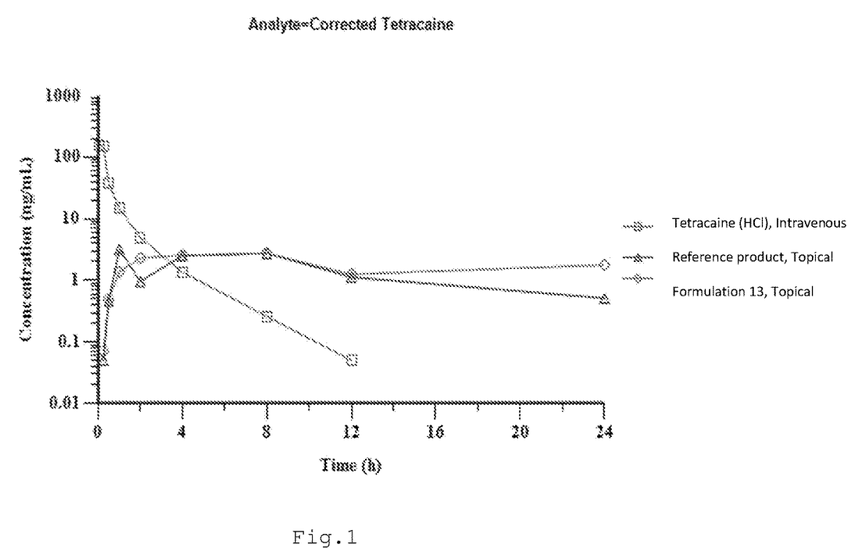
FIG. 1. The result of comparing the kinetic profile and bioavailability of tetracaine from Formulation 13 with respect to the reference product containing 7% tetracaine and intravenous administration.

The result of comparing the kinetic profile and bioavailability of tetracaine from Formulation 13 with respect to the reference product containing 7% tetracaine and intravenous administration is shown in FIG. 1.

Figure 2:
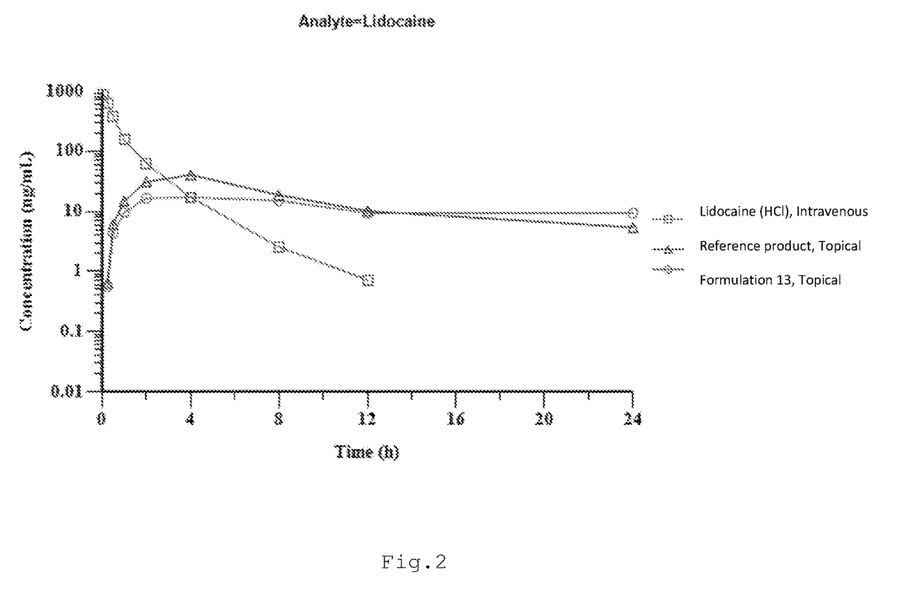
FIG. 2. The result of comparing the kinetic profile and bioavailability of Lidocaine from Formulation 13 with respect to the reference product containing 7% lidocaine and intravenous administration.

The result of comparing the kinetic profile and bioavailability of Lidocaine from Formulation 13 with respect to the reference product containing 7% lidocaine and intravenous administration is shown in FIG. 2

The concentration of the active substances, lidocaine and tetrazine, in Formulation 13 is 4% each, while in the reference product they are 78. The obtained results show that using lower concentrations of active substances, a similar or higher bioavailability of the used active substances was obtained. Also, the results obtained in the above study show that the active substances released from Formulation 13 show a stable blood concentration after 24 hours compared to the reference product.

The invention claimed is:

1. An anhydrous pharmaceutical ointment for the delivery of an anesthetic active substance, wherein said pharmaceutical ointment contains:
   at least one anesthetic active substance selected from the group consisting of lidocaine, tetracaine, prilocaine, benzocaine, bupivacaine, mepivacaine, and pharmaceutically acceptable salts thereof,
   a sulfoxide in the amount of 0.25% to 15% by weight of the ointment,
   a carbonic acid amide in the amount of 1% to 5% by weight of the ointment,
   propylene glycol in an amount from 5% to 15% by weight of the ointment,
   an aliphatic alcohol in an amount of 0.5% to 1.5% by weight of the ointment, an omega-9 monounsaturated fatty acid in an amount from 2% to 10% by weight of the ointment, and 50% to 69% by weight of a mixture of:
an anhydrous pharmaceutical ointment base and pork lard, wherein the weight ratio of the anhydrous pharmaceutical ointment base to the pork lard is from 1:2 to 2:1.

2. The pharmaceutical ointment of claim 1,
wherein the aliphatic alcohol is isopropyl alcohol and the weight ratio of isopropyl alcohol to propylene glycol is from 1:5 to 1:15; and wherein the sulfoxide is dimethylsulfoxide.

3. The pharmaceutical ointment according to claim 2, characterized in that it has a pH in the range of 8.5 to 10.5.

4. The pharmaceutical ointment according to claim 2, wherein the carbonic acid amide is urea.

5. The pharmaceutical ointment according to claim 2, wherein the omega-9 monounsaturated fatty acid is oleic acid.

6. The pharmaceutical ointment according to claim 2, wherein the anesthetic active substance is selected from the group consisting of lidocaine, tetracaine, and pharmaceutically acceptable salts thereof.

7. The pharmaceutical ointment according to claim 4, wherein the omega-9 monounsaturated fatty acid is oleic acid.

8. The pharmaceutical ointment according to claim 1, wherein the anhydrous pharmaceutical ointment base comprises at least 93.5% by weight white petrolatum.

* * * * *